(12) United States Patent
Bjerregaard et al.

(10) Patent No.: US 12,296,124 B2
(45) Date of Patent: May 13, 2025

(54) ENEMA NOZZLE COMPRISING RETENTION MEANS, AND AN ENEMA SYSTEM COMPRISING SAID ENEMA NOZZLE

(71) Applicant: Qufora A/S, Allerød (DK)

(72) Inventors: Henrik Bork Bjerregaard, Lynge (DK); Kristian Bjerg, Kokkedal (DK)

(73) Assignee: Qufora A/S, Allerød (DK)

( * ) Notice: Subject to any disclaimer, the term of this patent is extended or adjusted under 35 U.S.C. 154(b) by 0 days.

(21) Appl. No.: 18/839,081

(22) PCT Filed: Feb. 13, 2023

(86) PCT No.: PCT/EP2023/053434
§ 371 (c)(1),
(2) Date: Aug. 16, 2024

(87) PCT Pub. No.: WO2023/156322
PCT Pub. Date: Aug. 24, 2023

(65) Prior Publication Data
US 2025/0108158 A1    Apr. 3, 2025

(30) Foreign Application Priority Data
Feb. 16, 2022 (DK) ................................ 202270060

(51) Int. Cl.
*A61M 3/02* (2006.01)
(52) U.S. Cl.
CPC ................. *A61M 3/0279* (2013.01)
(58) Field of Classification Search
CPC ............. A61M 3/0262; A61M 3/0279; A61M 3/0295; A61F 2/0009; A61F 2/0013
See application file for complete search history.

(56) References Cited

U.S. PATENT DOCUMENTS

| | | | |
|---|---|---|---|
| 4,686,985 | A | 8/1987 | Lottick |
| 2011/0160657 | A1 | 6/2011 | Gobel |
| 2014/0358126 | A1 | 12/2014 | Gobel |
| 2020/0206411 | A1 | 7/2020 | Henry et al. |
| 2021/0059856 | A1 | 3/2021 | Eshel et al. |

FOREIGN PATENT DOCUMENTS

| | | |
|---|---|---|
| CN | 106964012 | 7/2017 |
| WO | 9707850 | 3/1997 |
| WO | 2020207547 | 10/2020 |

OTHER PUBLICATIONS

International Search Report and Written Opinion for International PCT Patent No. PCT/EP2023/053434 mailed Jun. 14, 2023 (17 pages).

*Primary Examiner* — Deanna K Hall
(74) *Attorney, Agent, or Firm* — Fox Rothschild LLP

(57) ABSTRACT

The present invention relates to an enema nozzle (1;18) for an enema system, and wherein said enema nozzle (1;18) comprises a catheter (2) provided with a flexible retention member (3;19) arranged for retaining the enema nozzle in a body cavity in a retention stage, and wherein said retention member is only partially filled with a liquid (15;21) in the retention stage. The combination of a flexible retention member (3;19) that is only partially filled with a liquid (15;21), ensures that the liquid contained in the retention member easily can be displaced/moved around inside the retention member (3;19) during use. In this way the retention member (3;19) remains pliable and flexible enough to be able to conform and adapt to the shape of the colon during use.

11 Claims, 3 Drawing Sheets

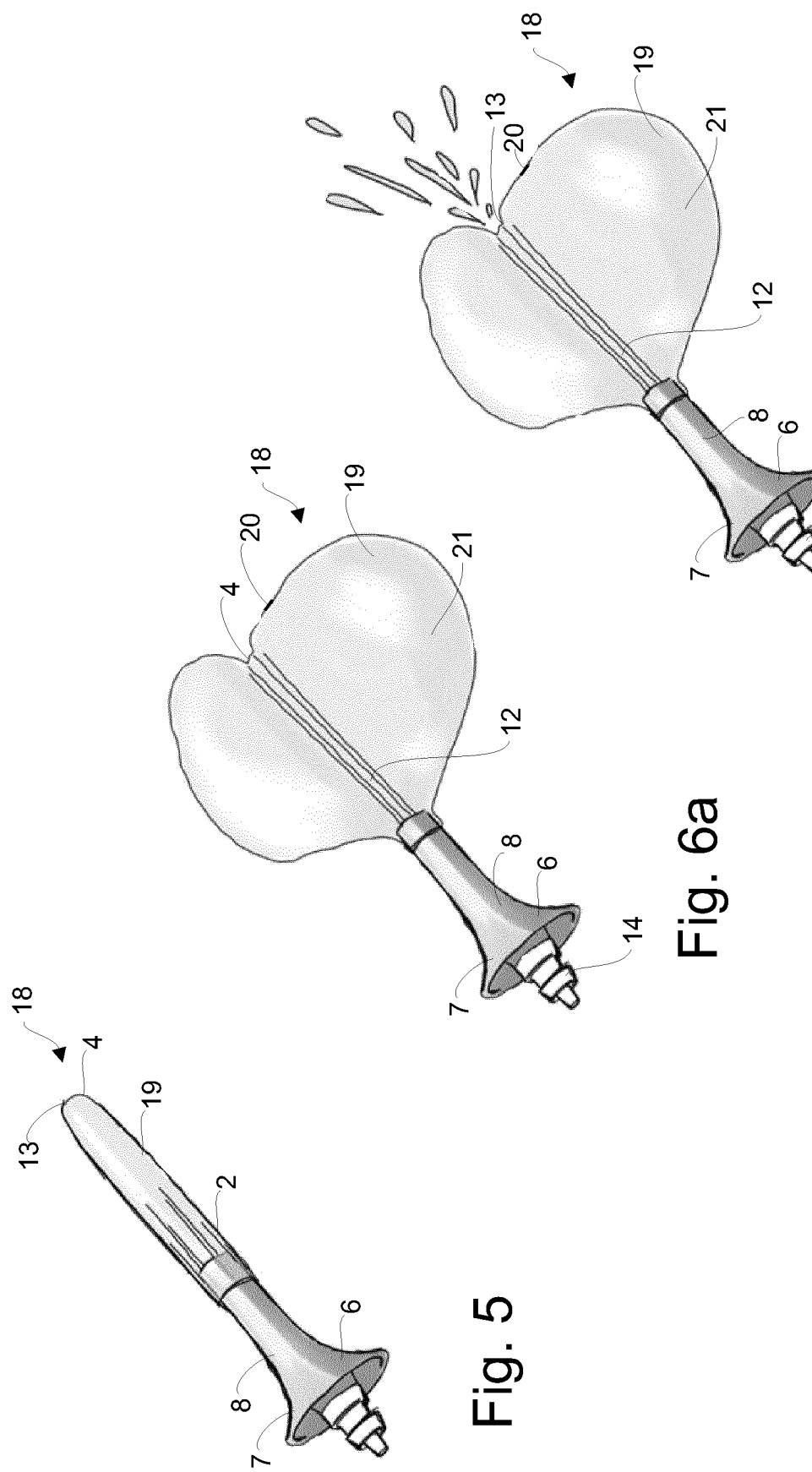

Figure 3:
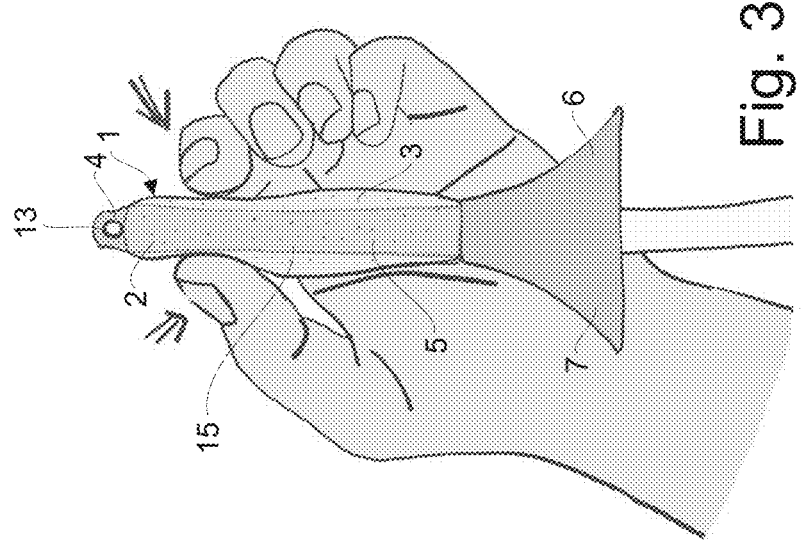

ENEMA NOZZLE COMPRISING RETENTION MEANS, AND AN ENEMA SYSTEM COMPRISING SAID ENEMA NOZZLE

CROSS REFERENCE TO RELATED APPLICATIONS

This application is a U.S. National Phase Application of PCT International Application No. PCT/EP2023/053434, filed on Feb. 13, 2023, which is an international application of and claims the benefit of priority to Danish Patent Application No. PA 2022 70060, filed on Feb. 16, 2022. The entire contents of these patent applications are herein incorporated by reference.

An enema nozzle comprising retention means, and an enema system comprising said enema nozzle.

The present invention relates to a enema nozzle comprising retention means, and an enema system comprising said enema nozzle.

Administrating an enema is a common medical procedure whereby fluid is injected into the rectum and lower intestine of a patient in order to induce bowel movement. The need for such a procedure typically arises in patients suffering from certain physical ailments in which voluntary bowel control is impaired or when the bowel needs to be cleaned before e.g. a coloscopy or a surgical operation.

Enemas are often administered to a patient at home when the need for medical assistance does not necessitate a doctor or another health care assistant. In this respect it is often difficult for the patient to administer the enema liquid to himself or herself since the conventional enema devices often causes discomfort and irritation when being inserted. Moreover, it is difficult for the patient to administer the liquid while steadily holding the enema nozzle in place during the procedure. Often another individual assists the patient but assistance may not always be available, if for instance, the patient lives alone.

In order to overcome these problems a number of enema devices comprise an inflatable balloon for retaining the nozzle in the rectum/colon during administration of the enema has been developed. Such a device is e.g. disclosed in U.S. Pat. No. 5,074,842 which describes an irrigation having a fixation balloon that is inflated using air, and wherein the air is delivered through a syringe valve communicating with an air passage. A similar system is known from European patent publication no. 1531885, which describes an irrigation device comprising a liquid reservoir and an air-inflated balloon for fixation of a tubular part inserted in the rectum.

Since air is used to inflate the balloon in these known devices, additional elements are needed in the devices in order to ensure that the air can be taken from the surroundings during the inflation procedure, and again vented to the surroundings (instead of into the body cavity) when the irrigation is completed. If the air in the balloon is delivered to the rectum and/or bowel before the nozzle is removed from the rectum, this result in an additional distention or dilation of the colon resulting in pain and discomfort for the patient. Furthermore, use of an air-filled balloon has the problem that the balloon will react to the body movements, e.g. peristaltic reflexes, whereby the nozzle inconveniently may be displaced causing leakage.

In order to overcome these drawbacks some enema devices, see e.g. WO2011023196, uses liquid to inflate the balloon. However, even though the balloon in this system will assist the patient by keeping the enema nozzle inside the rectum during the enema administration procedure, the inflated balloon becomes rigid/hard, and combined with the fact that the inflated balloon have a generally spherical form, the inflated balloon is without body adapting properties or able to mimetic the shape of the body cavity. Furthermore, if the balloon is overfilled the balloon may rupture causing damage to the fragile wall of the colon/rectum and leakage of the liquid filled content of the colon/rectum, and if the balloon is filled too little it cannot safely keep the enema nozzle in place during use. This is not only unwelcoming for the patient but also very demeaning, as the surroundings inevitability will be contaminated with irrigation liquid and bodily excretions if the enema nozzle unintentionally falls out. As some users of enema devices have no sensory function in the rectum they may not even register if the nozzle falls out.

It is therefore a first aspect of the present invention to provide an enema nozzle and an enema system that safely can be retained in the anal cavity and conform to the shape of said anal cavity during use.

It is a second aspect of the present invention to provide an enema nozzle and an enema system that will speed up the retention procedure and will demand less physical effort when using the enema system.

It is a third aspect of the present invention to provide an enema nozzle and an enema system that safely and effectively can be inserted and removed into a body cavity without causing harm and/or discomfort.

It is a fourth aspect of the present invention to provide an enema nozzle and an enema system that is inexpensive to manufacture and is simple and reliable to use, and therefore can be used for self-administration of an enema e.g. at home.

These and further aspects are achieved according to the present invention by providing an enema nozzle for an enema system, and wherein said enema nozzle comprises a catheter provided with a flexible retention member arranged for retaining the enema nozzle in a body cavity in a retention stage, and wherein said retention member is only partially filled with a liquid in the retention stage.

The combination of a flexible retention member and the fact that said retention member is only partially filled with a liquid, ensures that the liquid contained in the retention member easily can be displaced/moved around inside the retention member during use, e.g. when external pressure is applied to the sides of the retention member. In this way the retention member remains pliable and flexible enough to be able to conform and adapt to the shape of the colon, irrespectively of any deformations, e.g. hemorrhoids, fistulas, and/or abscesses in the colon. Furthermore, as the liquid can be displaced inside the retention member, said member will also provide a tight fit between the retention member and the colon/anal cavity. This will not only provide an effective seal, thereby preventing premature and unwanted leakage of fluid and fecal matter from the anus during an irrigation session, but also that the enema nozzle is capable of resisting forces applied by bodily fluids, waste and/or excrement that would tend to urge the catheter/enema nozzle out of the body opening after it has been inserted.

In contrast to the retention member of the present invention, the balloons used in convectional balloon catheters are completely or at least substantially completely filled with either liquid or air. Thus, the known balloons become hard and rigid, and if external pressure is applied to the sides of said inflated balloons, the balloons cannot be compressed and the liquid/air inside the balloon cannot be displaced.

Thus, conventional air/liquid filled balloons are not able to adapt to the shape of the colon in a similar way as the present invention.

Within the context of the present invention the term "partially filled" means that the retention member contains a liquid volume of 80% or less compared to the maximum volume of liquid the retention member can contain at its maximum stretching capacity. A person skilled in the art will know how to evaluate and determine the maximum volume of liquid by performing a number of experiments. One suitable experiment is first to measure the amount of liquid the retention member can contain before it reaches the retention members maximum stretching capacity, i.e. the size where the retention member cannot be stretched/expanded further, either because it will burst and/or break or because the retention member simply stops expanding, or cannot expand further. Just before the liquid added to the completely expanded retention member start to overflow, i.e. the retention member cannot contain any more liquid, or the retention member breaks/bursts, the maximum volume the retention member can contain is reached. Any volume which is 80% or less of said maximum volume is considered to be an amount within the term "partially filled". Thus, if the retention member burst at a volume of 50 ml water, then any volume of 40 ml or less will be considered to a "partially filled" volume.

Even though the retention member can contain at volume up to 80% of the maximum volume, it is preferred that the retention member contains a volume which is 60% or less, more preferred 50% or less, and even more preferred 40% or less, in order to provide a pliable, flexible retention member.

In a preferred embodiment the retention member does not comprise any air and/or other substances in gas-form when the retention member is placed in the retaining stage. It is thereby ensured that air/gas does not take up any space in the retention member, thereby improving the fluid dynamics when liquid is displaced inside the retention member. Furthermore air/gas would have the negative impact that it reacts to the body movements, e.g. peristaltic reflexes resulting in that the enema nozzle is less securely kept in place if the retention member contains air/gas.

It is furthermore preferred that the retention member in the retention stage is distended/stretched to 75% or less of the retention members maximum stretching capacity, thereby leaving space for the retention member to expanded when the liquid inside the retention member is displaced e.g. during insertion, or as a reaction to forces applied by bodily fluids, colon spasms, contractions and/or anal sphincter activity. It is in this respect preferred than the retention member only is distended/stretched to 60% or less, preferably 50% or less than the retention member's maximum stretching capacity.

The retention member is preferably made of a soft, flexible and/or expandable material, such as natural rubber, synthetic rubber, silicone, latex, urethane (polyurethane), polyvinylchloride, polyethylene, or any other expansible elastomer, polymer or other similar material.

The retention member may be of any shape, contour, size and volume; however the fixation member preferably has sufficient compliance to generally conform to the shape, contours, walls and structures of the respective body cavity, e.g. the rectum thereby exerting a compressive force. Also, male and female anatomy and subject size (e.g., adult vs. child) may dictate the shapes, contours, size and volume of the retention member.

In a preferred embodiment the retention member is a pouch or has an elongated pouch-like shape extending along the length of the catheter. Within the context of the present invention the term "pouch" refers to a bag or container arranged for containing the liquid. Said pouch may have any form and dimension as long as said pouch is capable of conforming to the shape of the anal cavity both when being inserted and when functioning as a retention member. It is furthermore preferred that the retention member is not formed as a sphere and/or has a substantially spherical or ellipsoid form, when the retention member is in the retention stage, i.e. when it contains the desired dosage of liquid for retaining the enema nozzle in the anal cavity.

In a preferred embodiment according to the invention, the retention member contains a predefined volume of liquid both before being inserted into a body cavity and when the retention member is placed in the retaining stage. Thus, in said embodiment the retention member contains the same volume of liquid before, during and after use, i.e. the retention member is arranged as a closed system wherein liquid neither can be added to the retention member nor removed from said retention member. However, since the flexible retention member is only partly filled with a liquid, the retention member is able to conform, and adapt to the body by allowing the liquid inside the retention member displaced during the insertion procedure according to the principals of fluid dynamics, e.g. by expanding certain areas of the retention member when the liquid is displaced to said areas. Thus, during insertion the liquid in the retention member will first be displaced towards the end opposite the inserting end, and when the catheter is fully inserted the liquid will be displaced towards the insertion end/tip due the external pressure from the sphincter, effectively providing both a seal with the anal cavity and retaining the enema nozzle in the anal cavity.

In a preferred embodiment the retention member has a predefined shape before use, and is preferably made of a material with an inherent shape memory, such that said retention member automatically will revert to its predefined shape, if possible.

In a preferred embodiment the retention member surrounds a section of the catheter and comprises an elongated stem part that via a smooth transition part extends into an expanded bulb part near the insertion end. It is preferred that retention member surrounds substantially the entire length of the catheter except, the tip of the catheter with the one or more delivery opening(s). In such an embodiment the liquid contained in the retention member will automatically be forced towards the expanded bulb part, unless pressure is applied to said bulb part e.g. during insertion in the anal cavity. Such an arrangement will both ensure that an effective seal is provided with the anal cavity, among others by the liquid remaining in the stem part that may form a seal with the anal opening, and that the enema nozzle is retained in the anal cavity via among others the bulb part.

In a preferred embodiment of the closed system, the retention member is made of a silicone, as said material is both flexible but still allows the retention member to have a predefined shape before use. It is accordingly preferred that the thickness of the silicone is between 0.3 and 1.0 mm, preferably between 0.3 mm and 0.5 mm, such as around 0.37 mm, as a silicone with said thickness provides an effective and durable system, in which the liquid easily can be displaced inside the retention member without having to worry about leaks and ruptures.

It is further preferred that the liquid inside the retention member, when said retention member is a closed system, is a viscous liquid, e.g. a polydimethylsiloxane (PDMS), or silicone oil, whereby the flow rate inside the retention member, i.e. how fast the liquid is displaced when pressure is applied to the sides of the retention member, is slowed down providing a more smooth insertion procedure in the anal cavity.

The inventors of the present invention have found that in order provide a smooth insertion, the viscous liquid preferably have a viscosity between 1 and 2000 Pa·S. For the sake of comparison, lotions typically have a viscosity within the range 1-30 Pa·s, while creams and ointments have a higher viscosity above 30 Pa·s, preferably above 80 Pa·s and below 150 Pa·s. In a preferred embodiment the viscous liquid has a viscosity within the range of 20-2000 Pa·s, preferably around 50-1000 Pa·s. All viscosities are measured using a Lamy VRM-08 viscometer with an MS DIN module at a temperature of 23° C. and at a shear stress of $0.8$ $s^{-1}$.

A person skilled in the art will understand that it is not always necessary to measure the viscosity of the viscous liquid in order to obtain a viscous liquid with the desired viscosity. It can also be determined by feel whether a viscous liquid has a viscosity suitable for use in the retention member. It should be noted that since the flow rate is inversely proportional to the viscosity, the flow rate of the viscous liquid can easily be adjusted, simply by adjusting the viscosity.

In an alternative embodiment the retention member is an open system wherein the retention member communicates with a liquid reservoir arranged for inflating the retention member with the liquid after insertion into the anal cavity.

The liquid may be delivered to the retention member in any conventional way; it is however relevant that the liquid volume delivered to the retention member is a liquid volume of 80% or less compared to the maximum volume of liquid the retention member can contain at its maximum stretching capacity, i.e. in the retention members fully expanded stage.

This will ensure, that the retention member according to the present invention, in contrast to the known retention members which becomes rigid after inflation with liquid (or air), remains pliable, soft and flexible also in the retention stage. This ensures that the retention member will continue to conform to the shape of the anal cavity e.g. if the user experiences increasing anal canal pressure, colon spasms, contractions and/or anal sphincter activity.

The retention member may in a preferred embodiment be made of a latex having a thickness between 0.05 mm and 0.1 mm, preferably around 0.08 mm. Said material is highly elastic and will accordingly easily conform and adapt to the anal cavity when liquid is delivered to the retention member.

In one embodiment the liquid flow in the enema nozzle is under the control of a control unit arranged to direct irrigation liquid from a liquid reservoir, either into the retention member, or into the flow channel and then out of the tip of the nozzle/catheter for administering the liquid to the anal cavity/bowel.

Said control unit is preferably arranged for in a first position transferring the irrigation liquid to the retention member, in a second position transferring the irrigation liquid to the flow channel of the catheter and in a third position discharging the irrigation liquid transferred to the retention member into the anal cavity e.g. via the flow channel.

When the control unit is set in the first position a fluid path between the reservoir and the retention member is established, ensuring that irrigation liquid expands the retention member by filling part of its lumen. The fluid path to the catheter is preferably not open. When the control unit is set in the second position, the path to the retention member is preferably closed simultaneously opening a liquid path to the catheter's flow channel from the reservoir, ensuring that irrigation liquid can be transferred from the reservoir to the flow channel without influencing the retention member.

When the control unit is set in the third position only a fluid path between the retention member and the flow channel is provided, whereby liquid present in the expanded retention member will be allowed to flow out via the flow channel and into the body cavity, thereby efficiently preventing any contamination of the surroundings. Furthermore, as liquid is used to expand the retention member the additional liquid from the fixation member will not cause any discomfort to the patient. When the retention member is deflated the catheter can be removed from the anal cavity without causing any discomfort.

In an advantageously embodiment the enema system according to the present invention comprises means for ensuring that the retention member cannot be filled with a liquid volume that exceeds the 80% of the maximum volume percentage of the retention member. Said means could e.g. be a pressure-sensitive valve, which will control the pressure inside the retention member, or a volume sensor for determining the amount of liquid transferred to the retention member.

In an alternative embodiment the retention member is arranged for being filled with a pre-defined dosage of liquid. Said pre-defined dosage may be transferred to the retention member by means of a delivery pump that is manually activated by the user, e.g. by squeezing a delivery pump in the form of a compressible bulb containing the predefined dosage. Said pre-defined dosage is preferably set to a volume which corresponds to 80% or less of the maximum volume percentage of the retention member, thereby in a simple and efficient manner ensuring that the retention member cannot be filled more than to a desired degree.

The rectum is a very sensitive area of the human body and must therefore be protected form abrasion, perforation, infection as well as excessive pressure. Thus, it is preferred that the retention member is deflated, at least to some degree, before being removed from the anal cavity.

Said deflating may e.g. be performed using a control unit as described above, however alternatively the retention member can comprise an outlet closed by a releasable closure. Said closure can be any kind of closure which is arranged for being opened to expel the liquid in the retention member into the anal cavity/bowel without compromising the function of the retention member.

In one preferred embodiment said releasable closure is a rupturable closure in the form of a membrane or welding providing a relatively faint joint which will be ruptured when pressure is applied on the retention member. This may e.g. be the situation when the enema nozzle is withdrawn from the anal cavity, displacing the liquid towards the insertion tip where it will gather until the pressure from the liquid forces the rupturable closure (membrane or welding) to break thereby allowing the liquid from the retention member to be expelled into the anal cavity.

In a different embodiment the releasable closure is an opening closed with a plug-like member, and wherein the plug-like member is connected with an operating device permitting opening of the opening without having to remove the enema nozzle from the anal cavity. Said operating device can e.g. be a string, that extends to the outside of the anal cavity, such that when the user applied a pulling force to said string, the plug will be released, whereby the liquid in the retention member will be free to flow into the anal cavity.

The enema nozzle according to the invention may have any desired shape and dimensions. However, since the catheter is arranged for being inserted into the anal cavity, said catheter is therefore preferably a substantially elongate tubular part. Said tubular part may in one embodiment have a proximal end that extends into a flared funnel-shaped part, preferably via a smooth transition. The flared funnel-shaped part is preferably arranged for providing a sealing effect with the rectum.

In order for the enema nozzle to deliver the irrigation liquid/enema to the anal cavity, the enema nozzle comprises a flow channel that extends/ends in one or more delivery openings near or at the catheter's distal tip.

The retention member is preferably surrounding a section of the catheter, and in a preferred embodiment the retention member retention member surrounds the catheter in substantially the entire length of the catheter, leaving only the tip of the catheter, with the delivery openings, free. It is furthermore preferred that the retention member, at least most of the retention member will be placed above the dentate line when placed in the retention stage, as this will prevent the retention member from irritating the sensitive nerve endings that may be positioned within the anal canal between the opening and the dentate line, also referred to as a pectinate line. In is in this respect preferred that the one or more delivery openings for expelling/delivering the enema is/are placed above the retention member, such that the enema is delivered to the colon above the retention member.

The flow channel is preferably arranged for being connected to any suitable delivery container, e.g. a delivery container in a large bed-side irrigation system for the use in medical or hospital facilities and/or a small compact delivery container for home-administration of enema. The nozzle may be removable connected to the delivery container by means of conventional coupling unit. Said coupling unit can e.g. comprise a first coupling part attach to the enema nozzle and a second coupling part attached to the delivery container for providing a fluid communication between the two parts. In an especially simple embodiment the first coupling part is the tube for the first flow channel and the second coupling part is a second tube on the delivery container. Said second tube is preferably adapted for providing a liquid tight fit together with the first tube in order to provide the coupling, e.g. by providing that at least one of the first and second tube is made of a flexible material, such that e.g. the one tube can be placed in the other tube.

The catheter may have any suitable length, depending on the intended delivery site of the enema in the colon, the longer the insertion part the further into the colon the enema may be delivered.

In one preferred embodiment the insertion body is relatively short i.e. arranged for delivering the enema in the areas just inside the rectum. In such an embodiment the length of the catheter is preferably less than 9 cm, preferably less than 7 cm and even more preferred around or less than 5 cm, such as down to 3 cm.

In order to further prevent any irritation and/or damage to the tissue during insertion/use, it is preferred that no sharp edges is present on the parts of the enema nozzle inserted into the body cavity, including any transition area between the retention member and catheter.

The retention member may be attached to the catheter in any suitable way, e.g. via glued or welding. It is however preferred that the enema nozzle is made using either 2K or 3K injection molding.

The simplicity of the enema system according to the invention ensures that any patient or user, e.g. an elderly person without undue efforts can use the enema nozzle for self-administrating irrigation liquid/enema. Since the retention member remains pliable, flexible and soft during use, and continues to conform and adapt to the users anatomy, the use of the enema nozzle according to the invention will significantly reduce the discomfort and inconvenience of the patient associated with the known systems.

Furthermore, at least the part of the enema nozzle intended for being inserted into the body cavity, including any exposed parts of the retention member, may be coated with a hydrophilic coating, for example either as a full coverage coating or an island coating consisting of hydrophilic dots separated by not-coated areas. When the hydrophilic coating gets wet, e.g. simply when contacted with water, saline or other liquid swelling medium prior to inserting the enema nozzle, the hydrophilic coating gels and/or swells and confers a friction-reducing surface to the exterior face of the coated section or coated part of the nozzle, thereby aiding in enabling a gentle insertion of the nozzle into e.g. the rectum. The swelled resilient and flexible and this hydrophilic coating is characteristic, together with the remaining liquid absorbing properties of the hydrophilic coating, makes the hydrophilic coating also act as an effective seal against leakage along the length of the tubular distal part and out of the rectum or other body cavity.

The enema nozzle may comprise other features, e.g. a number of one-way valves for preventing back flow into the nozzle etc.

Even though the enema nozzle and enema system according to the invention is intended for administering an enema to the colon via the rectum, the enema nozzle and device may also be used for irrigation, cleansing and/or infusion into other body cavity, e.g. artificial stomas and fistulas.

The invention will be explained in greater detail below, describing only exemplary embodiments of the enema nozzle with reference to the drawing, in which FIGS. 1-4 show a first embodiment of an enema nozzle according to the present invention, and FIGS. 5 and 6 show a second embodiment of an enema nozzle according to the present invention.

FIGS. 1-4 show a first embodiment of an enema nozzle 1 according to the invention. Said nozzle consists basically of a catheter 2 and a retention member 3 surrounding substantially the entire catheter 2 except the insertion tip 4 of the catheter. The catheter 2 further comprises a substantially elongate tubular part 5 defining an insertion part, and a proximal end 6 that extends into a flared funnel-shaped part 7 via a smooth transition 8.

The retention member 3 comprises an elongated stem part 9 that via a smooth transition part 10 extends into an expanded bulb part 11 near the insertion tip 4.

Figure 2:
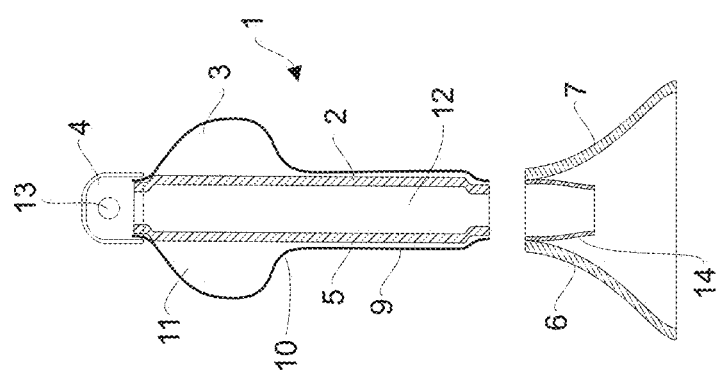
Figure 1:
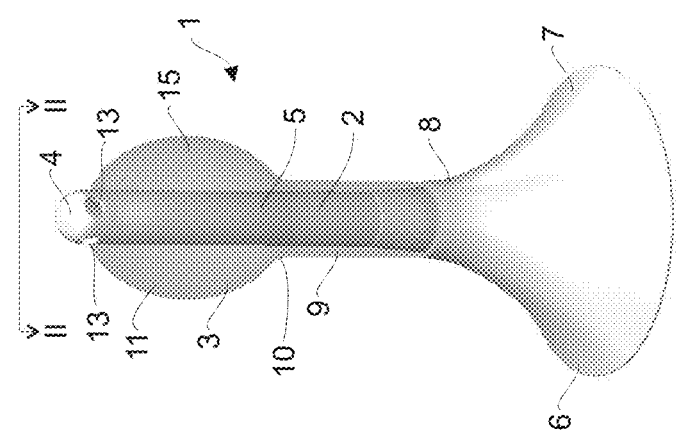

As best shown in FIG. 2, which is a cross-sectional view of FIG. 1 taken along the lines II-II, the enema nozzle 1 comprises a flow channel 12 that extends/ends in one or more delivery openings 13 near or at the inserting tip 4 for administering the enema to the rectum/colon. The nozzle is removable connected to a liquid reservoir (not shown), e.g. a hand held delivery pump by means of conventional coupling unit 14. Said coupling unit can be any conventional coupling unit, e.g. a snap fit.

In FIG. 2 the catheter 2 with the retention member 3 is separated from the funnel-shaped part 7 in order to shown that the retention member 3 extends along substantially the entire length of the catheter 2 except for the insertion tip 4 with the delivery opening(s) 13. The catheter 2 and funnel-shaped part 7 may be made in separate steps and connected to each other, e.g. by gluing or similar conventional means, after a liquid 15 is added to the retention member 3 and said retention member is sealed in order to provide a closed system of the retention member 3.

Thus, in the first embodiment shown in FIGS. 1-4, the retention member 3 is arranged as a closed system wherein liquid 15 neither can be added to the retention member 3 nor removed. Thus, the retention member 3 contains a predefined volume of liquid 15 which cannot change, i.e. the retention member 3 contains the same volume of liquid 15 before, during and after use. Said volume of liquid can be any suitable volume as long as the retention member 3 contains liquid in a volume of 80% or less compared to the maximum volume of liquid the retention member 3 can contain at its maximum stretching capacity.

In a preferred embodiment the retention member 3 is made of a soft silicon having a thickness of 0.3 to 1.0 mm, e.g. around 0.37 mm whereby the retention member 3 will have an inherent shape memory, i.e. it will return to its predefined shape when said retention member is not subjected to external forces.

In the embodiment shown in FIGS. 1-4 the retention member 3 contains about 10-30 ml of a liquid 15 in the form of a viscous liquid e.g. silicone oil with a viscosity of 1000 Pa·s measured using a Lamy VRM-08 viscometer with an MS DIN module at a temperature of 23° C. and at a shear stress of 0.8 $s^{-1}$. At the retention member's maximum stretching capacity, i.e. the point where the retention member 3 breaks or burst or stops stretching the retention member 3 can contain 90 ml, i.e. the maximum liquid volume of the retention member is 90 ml. A person skilled in the art will understand that the amount of liquid in the retention member can be varied at the production facilities to conform to the physical anatomy of different users, e.g. children and adults, the only requirement being that the retention member 3 is only partially filled, i.e. contains less than 80 vol % liquid.

The combination of a flexible retention member 3 that is only partly filled (between about 10 vol % and 33 vol % in the shown embodiment) with a viscous liquid 15 ensures that the liquid 15 retention member be contained in the 3 easily can displaced/moved around inside the retention member 3 during use, e.g. when external pressure is applied to the sides of the retention member 3. This is shown in FIG. 3, where the expanded bulb part is pressed by the fingers of a user, and the viscous liquid 15 is displaced/distributed via the principals of fluid dynamics to other parts of the retention member 3, which in response to said liquid displacement expand in the areas where the liquid is distributed to. In this way the retention member 3 remains pliable and flexible enough to be able to conform and adapt to the shape of the colon, irrespectively of any deformations, e.g. hemorrhoids, fistulas, and/or abscesses in the colon.

Figure 4C:
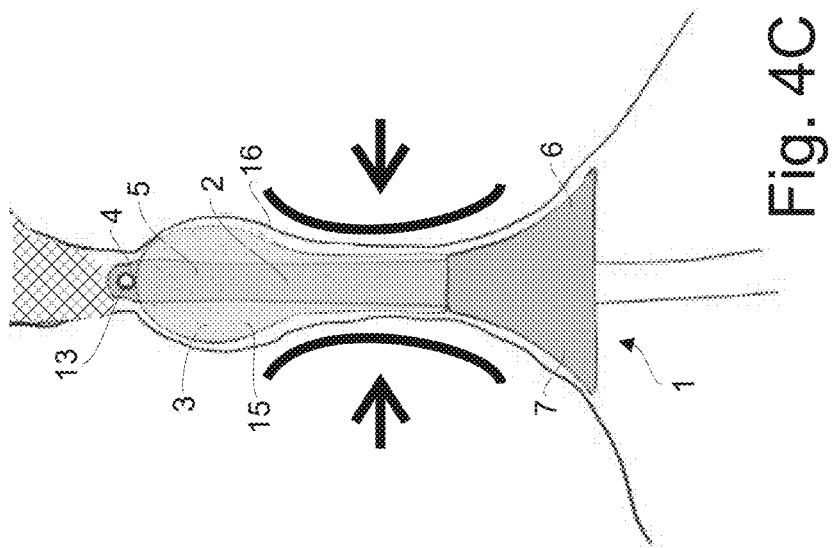
Figure 4B:
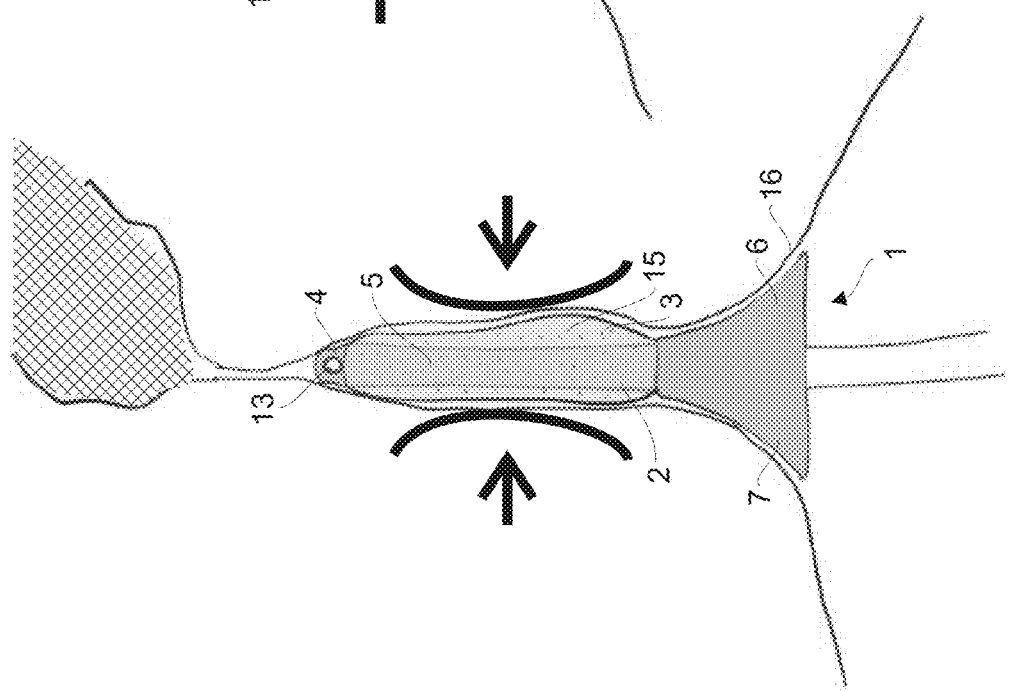
Figure 4A:
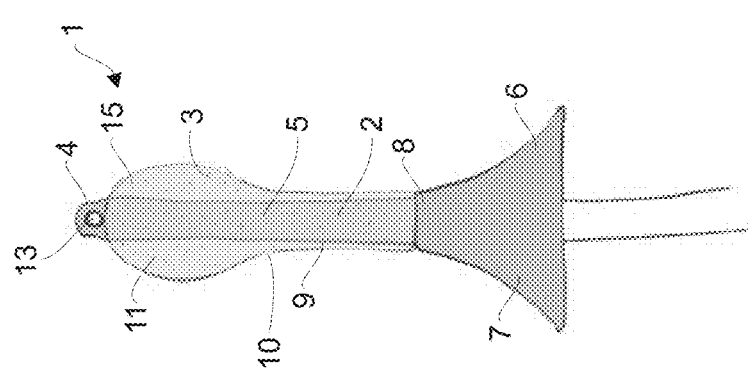

FIGS. 4a-4c shows the insertion of the first enema nozzle 1 in the anal cavity 16. In the position before use, see FIG. 4a, the retention member 3 has the predefined initial form, e.g. an elongated stem part 9 extending into a bulb part 11. When the catheter 2 is inserted into the anal cavity 16 the viscous liquid 15 in the retention member 3 will be displaced towards the catheter's proximal end 6, opposite the inserting tip 4, see FIG. 4b, and when the catheter 2 is fully inserted in the anal cavity 16 the liquid 15 will be displaced towards the insertion tip 4 with the bulb part 11 due the external pressure from the sphincter, and the inherent shape of the retention member 3. This will in combination effectively provide both a seal with the anal cavity 16 and ensure that the enema nozzle is secured in the anal cavity.

Thereafter the irrigation liquid can be administered to the anal cavity/bowel of the user from a liquid reservoir (not shown) in any conventional way via a suitable delivery tube 17. When the desired dosage of irrigation liquid/enema has been administered, the user can simply pull the enema nozzle 1 out, during which the viscose liquid 15 in the retention member 3 again will be displaced, allowing the retention member 3 to adapt, deform and/or fold by the internal forces of the colon/rectum wall during the removal process.

FIGS. 5 and 6 show a second embodiment of an enema nozzle 18 according to the present invention. Said enema nozzle corresponds to the first embodiment of the enema nozzle 1, and for like parts the same reference numbers are used. However, in contrast to the first embodiment, in which the retention member was a closed system, the enema nozzle of the second embodiment comprises a retention member 19 in the form of an open system, i.e. the retention member 19 communicates with a liquid reservoir (not shown) for inflating the retention member 19 with a liquid 21 after insertion into the anal cavity and/or for delivering the irrigation liquid to the anal cavity. The liquid reservoir can be connected to the enema nozzle via conventional coupling means 14, e.g. a snap fitting.

The retention member 19 surrounds the catheter 2 in substantially the entire length of the catheter 2, leaving the tip of the catheter free 4. One or more delivery openings 13 for administering the irrigation liquid are placed at the tip of the catheter.

The retention member 19 is preferably made of latex having a thickness between 0.05 mm and 0.1 mm, preferably around 0.08 mm. Said material is highly elastic and will accordingly easily conform and adapt to the shape, contours, walls and structures of the respective body cavity, e.g. the anal cavity when liquid is delivered to the retention member 19. It is in this respect preferred that the maximum liquid volume the retention member 19 can contain, at the retention member's maximum stretching capability, is around 1 liter or more, and that only between 10–50 ml is delivered to the retention member 19 in the retention stage, thereby providing a highly flexible and pliable retention member.

The second embodiment 18 according to the present invention has the advantage that the user can determined the amount of liquid 21 e.g. water or saline, delivered to the retention member, and accordingly the user can easily meet his/her own specific desires/requirements.

However, in order to ensure that the retention member 19 remains pliable, soft and flexible also in the retention stage, thereby ensuring that the retention member will continue to conform to the shape of the anal cavity e.g. if the user experiences increasing anal canal pressure, colon spasms, contractions and/or anal sphincter activity, the retention member 19 must not be filed with more than 80% of the maximum volume the retention member can contain at the maximum stretching capability. This may e.g. be done by connecting the retention member to a hand held squeezable delivery pump (not shown) comprising a pre-defined dosage of liquid e.g. water or saline, which is less than the 80%.

As is best seen in FIGS. 6a and 6b the filled retention member does not have well defined shape, as said retention member will conform to the user's anatomy.

After administration of the desired dosage of irrigation liquid/enema the retention member 19 must preferably be deflated in order to be removed without causing damage to the rectum/anal cavity.

In the embodiment shown the retention member 19 comprises a rupturable closure 20 in the form of a membrane providing a relatively faint joint which will rupture when pressure is applied on the retention member 19. When the user starts pulling the enema nozzle 18 out of the anal cavity, the liquid 21 inside the retention member 19 is displaced towards the insertion tip 4 where it will gather until the pressure from the liquid forces the rupturable closure (membrane) to break thereby allowing the liquid from the retention member to be expelled into the anal cavity.

Thus, when the user pulls the enema nozzle out of the anal cavity, the rupturable closure 20 will break, allowing the user to simply pull the enema nozzle 18 out of the rectum, during which the liquid 21 in the retention member 19 will be emptied into the anal cavity when being extracted, and fold in upon itself.

The enema nozzles 1, 18 may be connected to a substantially bulb-formed enema delivery container, arranged for containing the enema. The enema is administered by squeezing the delivery container one or more times, depending on the desired dosage.

The enema nozzles disclosed herein may also be used for larger irrigations systems wherein the enema nozzle is connected to the enema reservoir via a relatively long delivery tube, and wherein the irrigation system e.g. comprises pumping means, control means, collection means for the stool, etc.

Modifications and combinations of the above principles and designs are foreseen within the scope of the present invention.

The invention claimed is:

1. An enema nozzle for an enema system, and wherein said enema nozzle comprises a catheter provided with a flexible retention member arranged for retaining the enema nozzle in a body cavity in a retention stage, and wherein said retention member is only partially filled with a liquid in the retention stage wherein the retention member is arranged as a closed system such that liquid neither can be added to the retention member nor removed from said retention member, said retention member has a predefined initial form and comprises an elongated stem part that via a smooth transition part extends into an expanded bulb part, and wherein the retention member surrounds the entire length of the catheter except the tip of said catheter.

2. An enema nozzle according to claim 1, wherein the retention member contains a liquid volume of 80% or less compared to the maximum volume of liquid the retention member can contain at its maximum stretching capacity.

3. An enema nozzle according to claim 1, wherein the retention member contains a volume which is 60% or less, compared to the maximum volume of liquid the retention member can contain at its maximum stretching capacity, preferably a volume of 50% or less, and even more preferred a volume of 40% or less.

4. An enema nozzle according to claim 1, wherein the retention member does not comprise any air and/or substances in gas-form in the retention stage.

5. An enema nozzle according to claim 1, wherein the retention member in the retention stage is distended/stretched to 75% or less of its maximum stretching capacity, preferably to 60% or less.

6. An enema nozzle according to claim 1, wherein the retention member is made of a soft, flexible and/or expandable material, such as natural rubber, synthetic rubber, silicone, latex, urethane (polyurethane), polyvinylchloride, polyethylene, or any other expansible elastomer, polymer or other similar material.

7. An enema nozzle according to claim 1, wherein said retention member contains the same volume of liquid both before being inserted into a body cavity and when the retention member is placed in the retaining stage.

8. An enema nozzle according to claim 1, wherein the retention member is made of a silicone having a thickness of between 0.3 mm and 1.0 mm, preferably between 0.3 and 0.5 mm, such as around 0.37 mm.

9. An enema nozzle according to claim 1, wherein the liquid inside the retention member (4) is a viscous liquid, preferably having a viscosity within the range of 20-2000 Pa·s.

10. An enema nozzle (1;18) according to claim 1, wherein the retention member in the retention stage, does not have substantially spherical or ellipsoid form.

11. An enema system comprising the enema nozzle according to claim 1.

* * * * *